United States Patent [19]

Rajadhyaksha

[11] Patent Number: 4,762,549
[45] Date of Patent: Aug. 9, 1988

[54] DELIVERY OF PLANT GROWTH REGULATORS

[75] Inventor: Vithal J. Rajadhyaksha, Mission Viejo, Calif.

[73] Assignee: Nelson Research & Development Co., Irvine, Calif.

[21] Appl. No.: 484,027

[22] Filed: Apr. 11, 1983

Related U.S. Application Data

[63] Continuation-in-part of Ser. No. 429,931, Sep. 30, 1982, abandoned, which is a continuation-in-part of Ser. No. 310,948, Oct. 13, 1981, Pat. No. 4,525,199, which is a continuation-in-part of Ser. No. 725,490, Oct. 28, 1976, abandoned, which is a continuation-in-part of Ser. No. 588,247, Jun. 19, 1975, Pat. No. 3,989,816.

[51] Int. Cl.$^4$ ............................................. A01N 43/46
[52] U.S. Cl. ................................ 71/88; 71/94; 71/95
[58] Field of Search ..................... 71/94, 95, 88

[56] References Cited

U.S. PATENT DOCUMENTS

| | | | |
|---|---|---|---|
| 3,103,509 | 9/1963 | Schickh | 546/243 |
| 3,268,397 | 8/1966 | Williams | 546/243 |
| 3,977,860 | 8/1976 | Franz | 71/86 |
| 3,988,318 | 10/1976 | Copes et al. | 546/243 |
| 3,988,351 | 10/1976 | Copes et al. | 71/88 |
| 3,989,816 | 11/1976 | Rajadhyaksha | 424/274 |
| 4,310,525 | 1/1982 | Nelson | 8/564 |
| 4,311,481 | 1/1982 | Nelson | 424/244 |
| 4,359,334 | 11/1982 | Brown | 71/95 |
| 4,361,436 | 11/1982 | McCarthy et al. | 71/86 |

FOREIGN PATENT DOCUMENTS

| | | |
|---|---|---|
| 56261 | 7/1982 | European Pat. Off. |
| 857016 | 7/1949 | Fed. Rep. of Germany |
| 2029832 | 3/1980 | United Kingdom |

OTHER PUBLICATIONS

Alkawa et al., Chem. Abst. vol. 85 (1976) 1086z.
Zelinck et al., Chem. Abst. vol. 64 (1966) 9602o.
Nelson, Chem Abst. vol. 96 (1982) 105740b.
Nelson, Chem. Abst. vol. 96 (149181z).
Aikawa et al., Herbicidal Activity of Caprolactam Derivatives, J. Fac. Agr., Kyushu Univ. 20 75-78 (1976).
Chem. Abs. 9th Coll Index 1972-1976: 22902CS.
Anon.; Chem. Abs. 77: 26852X (1972).
Hull et al.; Chem. Abs. 76: 69110X (1972).
Steinbrunn; N-Substituted Lactams, Chem. Abs. 52: 10203i Abstract of German Patent No. 859,016.
Takematsa et al., Alkylprolidones as Herbicides; Chem. Abs. 84: 160605p (1976).
Takematsu et al.; Synergistic Herbicidal Activities; Chem. Abs. 83: 2325x (1975).
Rutten; Increasing the Water Solubility; Chem. Abs. 55: 19150c.

*Primary Examiner*—Catherine L. Mills
*Attorney, Agent, or Firm*—June M. Bostich

[57] ABSTRACT

The disclosure describes compositions and methods for improved delivery of plant growth regulators comprising contacting a plant with a composition comprising an effective amount of a plant growth regulator and an effective delivery enhancing amount of compound having the structural formula

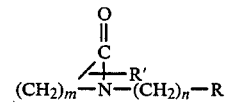

wherein R' is H or a lower alkyl group having 1-4 carbon atoms, m is 3-7, n is 0-17 and R is —CH$_3$,

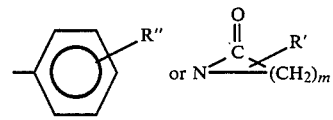

where R" is H or halogen, with the proviso that if m is 3 and R is CH$_3$, then n is 5-17.

4 Claims, No Drawings

DELIVERY OF PLANT GROWTH REGULATORS

REFERENCE TO EARLIER FILED APPLICATION

This application is a continuation-in-part of U.S. Application Ser. No. 429,931 filed Sept. 30, 1982, now abandoned which in turn is a continuation-in-part of U.S. Application Ser. No. 310,948 filed Oct. 13, 1981, now U.S. Pat. No. 4,525,199 which in turn is a continuatiion-in-part of the U.S. Application Ser. No. 725,490 filed Oct. 28, 1976, now abandoned, which in turn is a continuation-in-part of U.S. Application Ser. No. 588,247 filed June 19, 1975, now U.S. Pat. No. 3,989,816.

BACKGROUND OF THE INVENTION

1. Field of the Invention

The present invention generally relates to a method of treatment of plants. More particularly, the invention relates to an improved method of delivery of plant growth regulators.

2. Background of the Prior Art

The history of agriculture is the story of Man's attempts to modify plants and animals in order to produce more and better food. Plants (and animals) are capable of being extensively modified and Man has made use of this variability in his farming practice. In doing so he has made use of both 'nature' and 'nurture'—selecting and breeding from plants which have the most desirable characteristics and by cultural practices such as weeding, tilling, manuring, irrigating, pruning and disbudding he has provided the best conditions for the hereditary material of the desirable plants to realise their potential. Always of course he has been limited by the genetic makeup of the plant in question and breeding for desirable characteristics can often be a long, time-consuming, process and it may be years before the desired result is obtained. Now, however, with the introduction of chemical plant growth regulators a new dimension has been added to the possibilities of modifying plant growth and they offer the possibility of compensating for genotypic deficiencies that might take many years of breeding to alter by genetical methods.

Plant growth regulators are organic compounds, other than nutrients, that, in low concentrations, affect the morphological structure and/or physiological processes of plants. Plant hormones or phytohormones, are naturally occurring growth regulators that in low concentrations control physiological processes in plants. The synthetic growth regulators are used by Man to control such processes as fruit development, fruit thinning, defoliation, growth stimulation and retardation, rooting of cuttings and many other processes. Over the past 30 years the investigation and development of plant growth regulators has been one of the most active areas of fundamental and applied botanical research. The PANS Plant Growth Regulator Index (P. J. Kemp, 25 (2), 211 and 213) under the List of Common and Trade Names and Code Numbers has 492 entries (excluding herbicides except where these are used specifically for some growth regulatory purpose other than weedkilling).

Although ethylene has been used since the 1920's to ripen and fruit and auxins have been used to promote the rooting of cuttings, the development of plant growth regulators has been overshadowed by the development of herbicides. However, the immense amount of fundamental work that has been done on the naturally occurring auxins, the unfolding of the importance of ethylene as a plant hormone, the development of the gibberellins, the discovery of the cytokinins, the isolation of abscisic acid the synthesis of morphactins, and the development of growth retardants such as CCC (Cyclocel) have led to the recognition of the fundamental roles of the natural and practical applications of the synthetic plant growth regulators. Plant growth regulators that are in use in the United States at the present time affect a great variety of plant growth processes, including the following (some of the growth regulators in common use are in brackets): rooting of cuttings (indole-butyric acid); promotion of flowering in pineapples (1-naphthaleneacetic acid; B-hydroxyethylhydrazine; ethephon); prevention of preharvest drop of apples (NAA; daminozide); inhibition of turf growth (maleic hydrazide; mefluididediethanolamine); prevention of sprouting of potatoes (maleic hydrazide); floral induction in apple, pear, peach (succinic acid-2,2-dimethylhydrazine; 2,3,5-tri-iodobenzoic acid); early flowering of 'long day' plants, e.g. lettuce, radish, mustard, dill (gibberellins); flowering of many biennials which normally require low temperatures to flower (gibberellins); improvement of yield of sugar-cane by prevention of flowering (diuron; diquat); delay in flowering in almond and peach to avoid adverse weather conditions (daminozide); induction of abscission of mature citrus fruits (cyclohexim; 5-chloro-3-methyl-4-nitro-1H-pyrazole); defoliation of cotton leaves to aid harvesting of bolls (ethephon); thinning of fruit, e.g. grapes, peaches (gibberellic acid; ethephon; 3-chlorophenoxy-α-propionamide); prevention of pre-harvest drop of citrus (2,4-dichlorophenoxyacetic acid); induction of fruit set, e.g. in tomato, squash, eggplant, fig (4-chloro-phenoxyacetic acid; 2-naphthyloxyacetic acid); increase in size and quality of grapes (gibberellins); induction of amylase in barley for malting (gibberellins); stimulation of growth of sugar-cane (gibberellins); reduction of stem length in cereals (2-chloroethyl trimethylammonium chloride); development of female flowers, e.g. in pumpkins (NAA; ethephon; daminozide); promotion of male flowers, e.g. in hops (gibberellins); bioregulation of plant composition, e.g. colour in citrus, sugar in sugar-cane, vitamin content in vegetables, increase in dry weight, timing of crop development, increased latex from rubber trees (various growth regulators).

SUMMARY OF THE INVENTION

I have now discovered an improved method of delivery of plant growth regulators through the use of a compound which, when combined with a plant growth regulator, enhances the delivery of the plant growth regulator to the plant. The composition containing the delivery-enhancing compound and plant growth regulator may be applied to the plant in the conventional manner.

The invention, therefore, relates to an improved method of delivery of plant growth regulators comprising contacting a plant with a composition comprising an effective amount of a plant growth regulator and an effective, delivery-enhancing amount of a compound having the structural formula

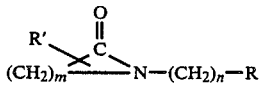

Where R' is H or a lower alkyl group having 1–4 carbon atoms, m is 3–7, n is 0–17, and R is —CH₃,

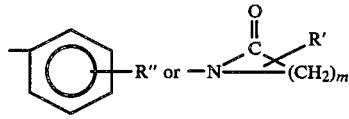

where R" is H or Halogen and R' has the same meaning as above.

The invention also relates to compositions comprising an effective amount of plant growth regulator and an effective, delivery-enhancing amount of a compound having the structural formula

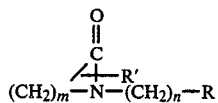

wherein R' is H or a lower alkyl group having 1–4 carbon atoms, m is 3–7, n is 0–17 and R is —CH₃,

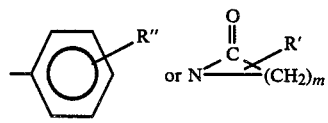

where R" is H or halogen, with the proviso that if m is 3 and R is CH₃, then n is 5–17.

In one preferred embodiment, R' is H, m is 5–7, R is CH₃ and n is 0–11. The preferred compound is 1-n-dodecylazacycloheptan-2-one.

DETAILED DESCRIPTION OF THE INVENTION

The 1-substituted azacycloalkan-2-ones used in this invention together with their methods of synthesis are disclosed in U.S. Pat. No. 4,316,893, the relevant portions of which are hereby incorporated by this reference.

The amount of 1-substituted azacycloalkan-2-one which may be used in the present invention is an amount effective for enhancing the delivery of a plant growth regulator to a plant. Generally, an effective amount ranges between about 0.01 to about 99.9 and preferably about 0.1 to 10 percent by weight of the composition.

Suitable plant growth regulators include both natural and synthetic auxins, such as IAA (indolyl-3-acetic acid), IBA (4-[indol-3 yl]butyric acid,), NAO (álpha-naphthylacetic acid), NOA (2-naphthyloxyacetic acid) and NAD (1-naphthylacetamide); phenoxyalkanoic acids, gibberelins, cytokinins, abscisic acid, maleic hydrazide, propham and cloropropham, S,S,S,-tributyl phosphorotrithioate, S,S,S,-Tributyl phosphorotrithioite, chloromequat, daminozide, glyphosine, ancymidol, chlorphonium chloride, dikegulac sodium, morpholinium chloride, fosamine, mefulidide, 4-methoxybenzophenones, PP 528 (ethyl-5-[4-chlorophenyl]-2H-tetrazol-2-yl acetate), piproctanyl bromide, 2-(3-aryl-5-pyrazoyl)benzoic acids, BTS 34723 (1-[N-2-phenoxyethyl)-N-propylcarbamoyl]-1N-imidazole), BTS 34442 (1-[N-2,4-dichlorobenzyl]-N-isopropylcarbamoyl-1N-imidazole), UBI P293 (2,3-dihydro-5,6-diphenyl-1,4-oxathiin), M&B 25,105 (propyl 3-t-butyl phenoxyacetate), thidaizuron (N-phenyl-N'-[1,2,3-thiadiazol-5-yl]urea), mepiquat (1,1-dimethyl-piperidinium chloride), BAS 09800W (mepiquat chloride plus ethephan), IZAA (5-chloroindazole-8-acetic ethyl ester), MON 8000, DOWCO 242 (tetraisopentyl-ammonium bromide), quarternary ammonium iodides; morphactins including chloroflurecol-methyl, flurecol-butyl, TIBA (2,3,5-tri-iodobenzoic acid); gametocides including RH 531 (sodium 1-[4-chlorophenyl]-1,2-dihydro-4,6-dimethyl-2-oxonicotinate), DPX-3778 (3-[4-chlorophenyl]-6-methoxy-1,3,5-triazine-2,4-dione triethanolamine) and allelopathins. Additional plant growth regulators are known in the literature, see, for example, Fletcher et al, *Herbicides and Plant Growth Regulators,* Chapter 2.

Opportunities for use of plant growth regulators include treatments for seed or seedlings for transplanting which will promote early growth and root development; substances to improve quality (usually protein levels and amino acid balance) of grain crops; substances to improve yield and quality of forages; opportunities in forestry, such as seedling survival and growth, early seed production and accelerated growth rates; systems to reduce energy costs by maximising response to cultivation, fertilisers (i.e. uptake, mobilisation, etc.) and irrigation water; compounds to inhibit ethylene action or production and thus reduce young fruit abscission in indeterminately fruiting crops; new gibberellins with species- or function-specific effects; new applications of known substances based on understanding hormone interactions and storage/inactivation systems ('slow release' compounds) and substances to manipulate natural conjugation reactions; substances to alleviate or minimise effects of plant diseases and insects or to facilitate systems of integrated pest management; substances to modify productivity by reducing photorespiration, dark respiration, or by promoting nitrogen metabolism/fixation, photosynthesis, translocation; substances that intensify synthesis of specific highly desired end-products (oil, protein, cellulose); substances to increase productivity by shifting developmental patterns, such as extending the period of inflorescence differentiation or seed development. The foregoing serves to illustrate the wide range of opportunities available to agricultural chemists.

Plant tissue culture pioneered by White, Steward, Skoog and others, beginning almost as a botanical curiosity, has with the help of growth-regulatory chemicals become a powerful tool in the hands of the plant breeder. It is now possible to tissue culture almost any plant and to develop uniform plantlets from such cultures. Even pollen grains can be used and the subsequent haploid plants made polyploid by the use of suitable chemical agents. Together with apical meristem culture there is an unending supply of material.

The method of application of the plant growth regulator composition described herein is conventional. See, for example, W. W. Fletcher and R. C. Kirkwood, *Herbicides and Plant Growth Regulators,* Granada publishing limited, New York, 1982.

The precise amount of the plant growth regulator composition to be delivered to the plant will obviously be an effective amount for the desired result expected therefrom. This, of course, will be ascertained by the ordinary skill of the practitioner. Due to enhanced activity which is achieved, the amount of plant growth regulator may often be decreased from that generally applicable. In accordance with the usual prudent formulating practices, a dosage near the lower end of the useful range of the particular agent may be employed initially and the dosage increased as indicated from the observed response.

I claim:

1. A method for delivering plant growth regulators to plants, comprising:
   contacting a plant with a composition comprising, as a first ingredient, a plant growth regulator; and
   enhancing the penetration of the plant growth regulator into the plant by including in the composition, as a separate, second ingredient, from 0.01% to 99.9% of the compound 1-n-dodecylazacycloheptan-2-one.

2. The method of claim 1, wherein the composition includes from about 0.1% to about 10% by weight of 1-n-dodecylazacycloheptan-2-one.

3. A composition, comprising:
   as a first ingredient, an effective amount of a plant growth regulator; and
   as a separate, second ingredient, from 0.01% to 99.9% by weight of the compound 1-n-dodecylazacycloheptan-2-one.

4. The composition of claim 3, wherein the second ingredient comprises from about 0.1% to about 10% by weight of the composition.

* * * * *